United States Patent [19]
Heagle et al.

[11] Patent Number: 5,290,449
[45] Date of Patent: Mar. 1, 1994

[54] BLOOD FILTER MATERIAL

[75] Inventors: David G. Heagle, Troutman; John J. Hiers, Elkin, both of N.C.

[73] Assignee: Lydall, Inc., Manchester, Conn.

[21] Appl. No.: 22,642

[22] Filed: Feb. 25, 1993

Related U.S. Application Data

[63] Continuation-in-part of Ser. No. 733,613, Jul. 22, 1991, Pat. No. 5,190,657.

[51] Int. Cl.$^5$ .................. B01D 39/02; B01D 39/04; B01D 39/06; B01D 39/08
[52] U.S. Cl. .................. 210/503; 210/504; 210/505; 210/508; 210/509; 428/283; 428/285; 428/286; 428/287; 428/323; 428/327
[58] Field of Search ............... 210/490, 505, 504, 508, 210/509, 500.36; 428/283, 284, 285, 286, 287, 323, 327, 288; 422/101; 264/122; 162/109

[56]        References Cited

U.S. PATENT DOCUMENTS

| | | | |
|---|---|---|---|
| 4,274,914 | 6/1981 | Keith et al. | 162/109 |
| 4,889,764 | 12/1989 | Chenoweth et al. | 428/283 |
| 4,904,343 | 2/1990 | Giglia et al. | 428/283 |
| 5,190,657 | 3/1993 | Heagle et al. | 210/645 |

*Primary Examiner*—Robert A. Dawson
*Assistant Examiner*—Sun Uk Kim
*Attorney, Agent, or Firm*—Griffin Butler Whisenhunt & Kurtossy

[57]        ABSTRACT

A filter material for filtering leucocytes from a fraction of or whole human blood, comprises a textile web having a thickness of between about 2 millimeters to about 12 millimeters and a bulk density of about 0.05 to 0.4 g/cm$^3$. The web has a plurality of interlocked textile fibers with average deniers between about 0.05 and 0.75 and average lengths between about 3 millimeters and 15 millimeters. The textile fibers are distributed in the web to form a matrix thereof with spaces between adjacent interstices of interlocked fibers. A plurality of fibrillated particles of textile fiber material, having a surface area of between 5 and 100 square meters per gram are disposed within the spaces of the matrix. The weight ratio of the fibrillated particles to the textile fibers is between about 1:99 and 40:60. A plurality of glass fibers, having an average diameter of between 0.1 and 5 microns and being about 2% to 85% of the web, also form part of the matrix. A thermoplastic binder is disposed at least at cross-over portions of the matrix textile fibers and matrix glass fibers, with the amount of the binder being about 0.1% to 20% by weight of the web.

26 Claims, 2 Drawing Sheets

BLOOD FILTER MATERIAL

This application is a continuation-in-part of prior U.S. application Ser. No. 07/733,613, filed on Jul. 22, 1991, now U.S. Pat. No. 5,190,657 issued Mar. 2, 1993, the entire disclosure of which is incorporated herein by reference and relied upon for disclosure.

BACKGROUND OF THE INVENTION

The prior application discloses a blood filter and method of filtration for removal of leucocytes from whole blood or blood fractions. The filter material is a shape-sustaining laid textile web having a thickness of at least about 1 millimeter and a bulk density of between about 0.05 and 0.4 g/cm$^3$. The web has a plurality of interlocked, textile fibers with average deniers between about 0.05 and 0.75 and average lengths between about 3 millimeters and 15 millimeters. The textile fibers are substantially uniformly distributed in the web so as to form a matrix of the fibers with spaces between interstices of the interlocked fibers. Within those spaces are disposed a plurality of fibrillated particles of polymeric material having a surface area of between about 5 and 60 square meters per gram. The fibrillated particles have a plurality of fine fibrils which are interlocked with adjacent textile fibers such that the fibrillated particles are not substantially displaceable from the web during filtration of blood. The weight ratio of fibrillated particles to textile fibers is between about 1:99 and 40:60.

As can be appreciated, the textile fibers and the fibrillated particles must be so interlocked that significant amounts of fibers or fibrillated particles are not displaced from the filter material during filtering of blood, since displaced fibers or particles remain in the filtered blood. A significant amount of displaced fibers or fibrillated particles in the filtered blood could cause difficulties when the filtered blood is transfused into a human patient.

As disclosed in that application, for efficient and effective depletion of leucocytes from blood passing through the filter material, both the fiber geometry and the surface area of the fibers are important, and that, very importantly, the surface area must be significantly greater than the usual prior art blood filters, since otherwise the degree of leucocyte removal is not sufficient. Further, since fiber geometry and surface area are important for leucocyte depletion, the depth (thickness) of the filter material is also important. Somewhat similarly, since the bulk density of the filter material and the denier of fibers affects fiber geometry and surface area, these are also important.

However, to achieve the high surface area of the filter material required for effective leucocyte removal from blood, a critical component is that of the very high surface area fibrillated particles in the filter material. Ordinary textile fibers cannot provide such high surface areas to the filter material which surface area is required for high leucocyte removal. The fibrillated particles are somewhat elongated particles with an elongated central portion from which radiate a large number of fibrils. Generally speaking, a typical particle has an overall length of less than 1000 microns, e.g. 5–300 microns, and a width and depth of from about 0.1 to 50 microns, e.g. 0.1 to 5 microns.

As can be appreciated, it is important to ensure that the very small fibrillated particles are not significantly displaced from the filter material during filtration of blood, and, as disclosed in that prior application, this is achieved by interlocking the fibrils of the fibrillated particles with adjacent matrix textile fibers. In addition, the depth (thickness) of the filter material, the bulk density thereof and the length of the matrix textile fibers (which affects the configuration of the laid matrix textile fibers) contribute to retaining the fibrillated particles. Further, especially at higher weight ratios of fibrillated particles to matrix textile fibers, e.g. 6:94 to 10:90, permanent securing of the fibrillated particles in the filter material may be improved by use of means for adhering the matrix textile fibers and fibrillated particles to each other, such as by tackifying adhesives and especially the use of sheath/core fibers for at least part of the matrix textile fibers, e.g. a sheath of low melt temperature polymer and a core of higher temperature polymer. When the matrix textile fibers are at least in part such sheath/core fibers, during usual processing of the filter material web, the sheath softens and causes bonding, upon cooling, between the matrix textile fibers themselves and fibrillated particles, especially the fibrils thereof.

SUMMARY OF THE INVENTION

While the filter materials of that prior application, as very briefly described above, are quite effective for leucocyte removal from blood or blood fractions, it has not been found that the overall performance of those filter materials may be further improved in certain regards by use of certain modifications thereof. In this regard, it has been found that the efficiency of the filter material (percent leucocyte removal per unit thickness of filter material) can be improved. This means that for a targeted leucocyte removal percentage, the present improved filter material can be of less thickness than the filter material of the prior application. This, in turn, means that the amount of blood or blood fractions retained in the filter material after filtration is completed is less than that of the filter material of the prior application. While this difference in the amount of retained blood is not an absolute large amount, the difference can be quite important, especially in certain filtrations of blood.

Further, with the present invention, less fibers are released from the filter during an AAMI test (defined in Example 3) which is a very severe test, i.e. more severe than in practical use, but this well recognized test ensures a substantial safety factor for actual use of the filters.

In the above regard, the present invention is based on several primary and several subsidiary discoveries. First of all, as a primary discovery, it was found that if the average sizes (diameter and length) of the matrix fibers are, generally speaking, less than the average sizes of the matrix fibers of the prior application, increased efficiency of the filter material occurs. As a subsidiary discovery, it was found that this is especially true when the matrix fibers are, at least in part, made of certain materials, especially glass.

As a second primary discovery, it was found that these smaller average matrix fibers could nonetheless adequately interlock with the fibrillated particles to prevent displacement of either the matrix fibers or fibrillated particles from the filter material during blood filtration when the filter material has therein an added thermo-softening binder.

As a subsidiary discovery in the above regard, it was found that certain binders could be added to the web of matrix fibers and fibrillated particles, and the web could then be heated to uniformly distribute these binders and set the binder in such a manner as to interlock the smaller average matrix fibers and fibrillated particles so that no significant amount thereof is displaceable from the filter material during filtration of blood or blood fractions.

As a primary discovery, with such binders, fibrillated particles of larger surface area may also be used and the efficiency of the filter material (and hence the required thickness of the filter material for a targeted leucocyte removal) could further be reduced. As a subsidiary discovery, smaller average matrix fibers may be used with the larger surface area fibrillated particles, when such binder is used, to provide very high efficient filter material.

Thus, briefly stated, the present invention provides an improved filter material for filtering leucocytes from a fraction of or whole blood comprising a shape-sustaining laid textile web having a thickness of at least about 1 millimeter and a bulk density of between about 0.05 and 0.4 g/cm$^3$. The web has a plurality of interlocked textile fibers with average deniers between about 0.05 and 0.75 and average lengths between about 3 millimeters and 15 millimeters. The textile fibers are substantially uniformly distributed in the web so as to form a matrix of the textile fibers with spaces between adjacent interstices of interlocked fibers. A plurality of fibrillated particles of polymeric material having a surface area of at least five square meters per gram (but preferably less than 100 square meters per gram) are substantially disposed within the spaces of the matrix, and the weight ratio of the fibrillated particles to the textile fibers is between about 1:99 and 40:60.

The web also has therein a plurality of glass fibers (forming at least a part of the matrix fibers) having an average diameter of between about 0.1 and 5 microns and the amount of the glass fibers is about 2% to 85% by weight of the web.

The web has added thereto a thermoplastic binder disposed at least at cross-over portions of the textile fibers and the glass fibers and the amount of the binder is about 0.1 to 10% by weight of the web.

The binder is preferably applied to the formed web as an emulsion thereof.

DETAILED DESCRIPTION OF EMBODIMENTS OF THE INVENTION

Figure 1:
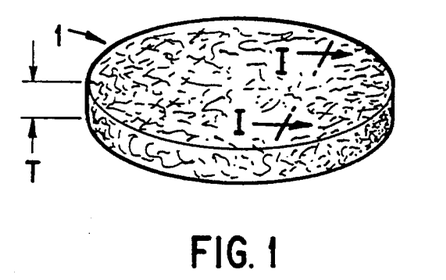
FIG. 1 is a perspective view of the filter made of the present material, in a configuration useful for placing in a filter carrier.

The present invention provides a filter material for filtering leucocytes from a fraction of or whole human blood. FIG. 1 shows such a filter made of such material. That filter, generally 1, is made from a filter material which is a shape-sustaining laid textile web. As shown in FIG. 1, the web has been cut in a circular configuration to form the filter, and the filter is suitable for loading into a cylindrical filter carrier. In this regard, the term "laid" is used in its ordinary technical sense. Thus, the web must be either air laid or wet laid, as opposed to, for example, needled, since it is in the laying process that the textile fibers, glass fibers and the fibrillated particles so interlock that the glass fibers and fibrillated particles are bound into the filter material. Needled textiles, for example, cannot provide such interlocking of the glass fibers and fibrillated particles with the textile fibers, and it is, therefore, necessary that the web be a laid web.

The thickness T of that web must be at least 1 millimeter, most preferably at least 2 millimeters, and may be up to about 30 millimeters, or more. A filter depth, as opposed to a web depth, results from placing layers of filter webs one upon another, until the desired filter depth is achieved. Thus, if a filter depth of, e.g., 12 millimeters, is desired and the web has a depth of 2 millimeters, six such layers of web will be required. Thus, rather than producing thick webs which are more difficult to product, thinner, more easily produced webs are preferred, with an appropriate number of layers of web to achieve the desired filter thickness.

However, for effective leucocyte depletion from a blood fraction or whole blood passing through the filter, there must be sufficient depth of the filter that the leucocytes have an opportunity to be significantly retained within the filter, both by the geometry of the fibers and by the surface area of the fibers and fibrillated particles. In this regard, a 1 millimeter filter depth (1 millimeter thickness of the filter material) is considered to be the about the minimum effective depth, since, at this depth, about 70% of leucocytes will be depleted from the blood passing therethrough, and a 70% to 75% depletion is considered about the minimum depletion for effective filtration of leucocytes, although some depletion will occur with lesser depths.

However, if the depth of the filter is about 2 millimeters, then the depletion percentage of leucocytes increases to about 80% to 85% or more. When the depth of the filter is about 6 millimeters, the percentage of depletion of the leucocytes increases to about 99%. When the depth of the filter is about 8 millimeters, the depletion of the leucocytes is at least 99%. However, at about 15 millimeters depth, the pressure drop through the filter when filtering blood begins to significantly increase. That increase in pressure drop continues as the filter depth increases and the pressure drop becomes greater than that which would be desired for ordinary filtration of blood with filter depths above about 20 millimeters. It is for these reasons that the filter depth is usually between about 2 and 20 millimeters, although greater than 20 millimeters and up to about 30 millimeters may be used in special cases where the pressure drop is not of concern and depths of only about 1 millimeter may be used where leucocyte filtration is not the primary concern. Filter depth is also important in regard to percentage of leucocyte depletion as a function of blood throughput. For example, if the thickness is too small, the filter may start with, for example, a 99% depletion for the first 200 mls of blood, but drop to 94% depletion for the next 200 mls of blood.

The overall bulk density of the filter material must be between about 0.05 and 0.4 g/cm$^3$. As can be appreciated, the density of the filter material relates to the fiber geometry, and, as noted above, the fiber geometry plays an important role in both the depletion of leucocytes and in ensuring that the fibrillated particles are firmly and securely locked in the filter material. This density is the density of the laid web (on a dry basis) but before the binder is added thereto, and also does not include fillers or the like and does not include any purposeful compression of the web other than as described below. At densities significantly below 0.05, the amount of fibers in the filter material is simply not sufficient to ensure a large number of interstices between the fibers for securely locking the fibrillated particles into the filter material. At a density above about 0.4, the amount of fibers to ensure such locking of the fibrillated particles has been exceeded, and the additional density simply results in increased pressure drop, without any significant further benefit to the filter material. Therefore, the density of the laid web must be between about 0.05 and 0.4 g/cm$^3$.

As can be easily appreciated, the density of a laid web of fibers depends on the method of measuring that density, since a thickness measurement must be made to calculate density and the thickness is open to interpretation. Ordinarily, with textile webs, the thickness is measured after a weight is placed on the web to provide a clear upper edge. This weight can vary with the particular filter material, and it is only necessary to have sufficient weight to provide a clear upper edge, but generally a weight of between about 0.5 to 1 lb. per square inch will provide such a clear upper edge.

Figure 2:
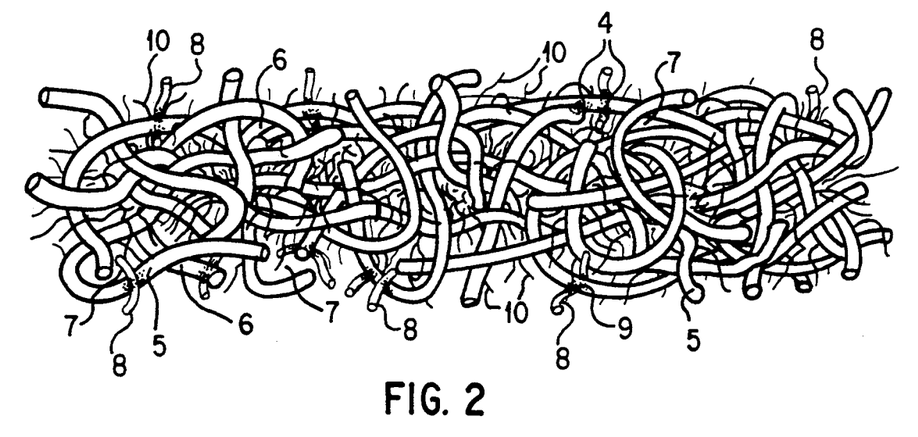
FIG. 2 is a highly diagrammatic partial cross-sectional view of a portion of the filter of FIG. 1, taken along lines I—I.

As seen in FIG. 2, which is a highly diagrammatic illustration of a portion of a section of the filter of FIG. 1, the filter material is comprised of a plurality of matrix textile fibers 5. In this regard, the present filter material provides high leucocyte depletion because the matrix textile fibers keep the fibrillated particles separated so that the high surface area thereof is not obscured or reduced due to coalescing or compacting.

The average denier and length of the matrix textile fibers could result from a mixture of very low denier or short fibers and very high denier or long fibers, but this is not the intention, since this would not achieve the fiber geometry described above. Accordingly, to provide an acceptable average length and average denier, at least 60% of the matrix textile fibers will have lengths and deniers within about 3 to 15 millimeters and about 0.05 and 0.75 denier ranges, and preferably at least 70% and more preferably at least 80 to 85% will be within these ranges.

As noted above, it is necessary to ensure that the matrix textile fibers are substantially uniformly distributed in the web, so that, correspondingly, the interstices are uniformly distributed and uniformly lock the matrix glass fibers and fibrillated particles in the filter material. In this regard, the matrix textile fibers must be so interlocked together that the matrix glass fibers and fibrillated particles are, in turn, so interlocked to the matrix textile fibers that the filter material can withstand a filtering blood pressure drop of at least two feet of head without substantial displacement of the matrix glass fibers or fibrillated particles from the web.

As can be seen in FIG. 2, the matrix textile fibers 5 are substantially uniformly distributed through the web so that as to form a matrix of the textile fibers. That matrix has spaces 7 between adjacent interstices 6 of the interlocked matrix textile fibers 5 and the matrix glass fibers 8. Within these spaces, there are a plurality of fibrillated particles 10 of very high surface area, including the surface area of the fibrils 11 of the fibrillated particles 10 (see FIG. 3). Those fibrillated particles 10 are disposed within spaces 7, as well as along and among the matrix textile fibers 5 and the matrix glass fibers 8, so as to provide the high overall fiber surface area of the filter material. In this regard, fiber surface area refers to the area of the surface of all of the matrix textile fibers 5 and matrix glass fibers 8 and the fibrillated particles 10, including the fibrils 11 thereof, within the filter material.

As a bench mark, conventional filters, even with very fine textile fibers, may have a total surface area of all fibers of perhaps 0.5 square meters or even perhaps about up to one square meter per gram, although, usually, the total surface area will be much less. Even with non-textile fibers, such as meltblown fibers used in prior art filters, surface areas of only about one square meter per gram can be obtained. In contrast, the total surface area of all fibers and fibrillated particles in the present invention will be at least one and one-half times that surface area and more usually at least two to three or four or five times that surface area, e.g. a total surface area of at least about 1½ square meters per gram.

Figure 3:
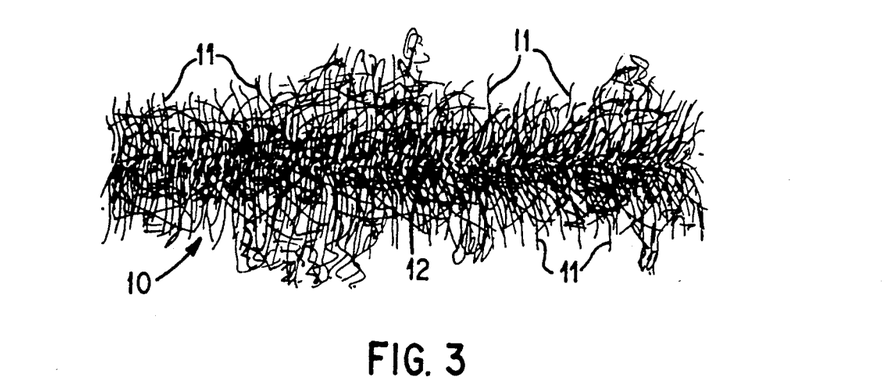
FIG. 3 is a highly diagrammatic illustration of a portion of the fibrillated particle of textile fiber material, used in the present invention.

As highly diagrammatically shown in FIG. 3, the fibrillated particles 10 have a plurality of fine fibrils 11 which extend and radiate from some generally elongated central portion 12 of the fibrillated particles 10. Those fibrils, as diagrammatically shown in FIG. 2, interlock among the matrix textile fibers 5 and the matrix glass fibers 8, and particularly in the interstices 6 between the fibers. Thus, by wrapping the fibrils 11 around the matrix textile fibers 5 and matrix glass fibers 8, and especially by the fibrils 11 being interlocked between matrix textile fibers 5 and matrix glass fibers 8 at interstices 6 thereof, the fibrils 11 are securely interlocked with the matrix textile fibers 5 and matrix glass fibers 8 such that the fibrillated particles 10 are not substantially displaced from the filter material during filtration of blood.

A typical fibrillated particle is an elongated particle, as shown in FIG. 3 by the illustrated portion of a particle, with an elongated central proportion 12 and radiating fibrils 11. A length, width and depth of such a particle is, quite apparently, difficult to accurately measure or specify, but for understanding purposes, fibrillated particles have a general overall length of less than 1000 microns, e.g. 5 to 300 microns, but more usually somewhere about 5 to 50 microns. The width and depth vary considerably along the length of the central portion 12 and vary from 0.1 micron or below to 50 microns, but, generally, the widths and depths are between about 0.1 and 5 microns, and more usually between 0.2 and 0.7 micron.

From the above dimensions, it will be appreciated that a particular fibrillated particle 10, as shown in FIG. 2, can be so long that it actually weaves in and out of spaces 7 and one fibrillated particle may serpentinely lie in a number of spaces 7, e.g. up to 100 of such spaces 7. Thus, such a fibrillated particle, and especially the fibrils 11 thereof, has a multitude of interstices 6 with which to interlock and a large number of matrix textile fibers 5 and matrix glass fibers 8 about which serpentinely wrap. This makes a very secure deployment of the fibrillated particles and, thus, ensures that the fibrillated particles will not be displaced during normal filtration of blood or a blood component.

On the other hand, from the above dimensions, it will be appreciated that a particular fibrillated particle may essentially lie within a single space 7 bounded by adjacent interstices, with the fibrils 11 wrapped around adjacent matrix fibers and locked between adjacent matrix fibers forming adjacent interstices. Also, a particular fibrillated particle may be of any intermediate size between the two sizes discussed above, and combinations of such locking of the fibrillated particles will occur.

The weight ratio of the fibrillated particles to the matrix textile fibers must be between about 1:99 and 40:60, and especially between about 5:95 and 40:60, and preferably about 20:80. If that ratio is less than about 3:97, the additional surface area supplied by the fibrillated particles is marginal for desired leucocyte filtration, and at below about 1:99, the surface area is simply not sufficient to achieve a minimum desired depletion of leucocytes, i.e. at least a 70% depletion. With increasing ratios of fibrillated particles to textile fibers, the depletion of leucocytes from blood will be correspondingly increased, such that at a ratio of about 5:95, the depletion percentage will be close to about 90%, and at about 10:90, the depletion will be about 99%. However, with increasing ratios, it will be appreciated that the number of matrix textile fibers, and the interstices formed thereby, will be correspondingly decreased, and there may not sufficient matrix textile fibers to keep the fibrillated particles separated. Therefore, high percentages of fibrillated particles results in lower average pore size and increased flow resistance without any increase in leucocyte depletion. Further, at a ratio of about 40:60, the number of matrix textile fibers in the filter material is decreased to the point where it is no longer reliable that most of the fibrillated particles will be separated, and it is for this reason that the ratio of fibrillated particles to matrix textile fibers should not exceed about 40:60, particularly should not exceed about 30:70, especially 20:80.

All of the foregoing, of course, depends somewhat on the amount of matrix glass fibers 8 in the filter material, as well as the particular sizes of thin matrix glass fibers. As noted above, the amount of glass fibers can be as low as about 2% by weight of the filter material web, and quite obviously, at this low percentage, the above will remain essentially correct. However, as also noted above, the amount of matrix glass fibers 8 in the filter material web may be as high as 85% and also, quite obviously, at this higher percent the above will not be correct, without correcting for the glass fiber content. Thus, especially at these higher percentages of matrix glass fibers 8, the ratio of fibrillated particles to matrix textile fibers could be reduced from 3:97, e.g. all the way down to the lowest limit of 1:99, and still provide sufficient surface area. However, it has been found that for the present improvement the above ratios may still be followed, although there is more permissible latitudes in connection therewith as a result of the presence of the matrix glass fibers.

The glass fibers 8, as noted above, should have an average diameter of between about 0.1 and 5 microns. These are, of course, very fine non-textile fibers. Preferably, the average diameter will be between about 0.3 and 2.0 microns and especially between about 0.5 and 1 micron.

The glass of the fibers may be any conventional glass, such as E-glass, S-glass, borosilicate glass, etc. Further, many conventional ceramic fibers have essentially glass-like physical properties, as opposed to mainly ceramic properties. Thus, ceramic fibers (not based on silica) may be used when those ceramic fibers have glass fiber-like physical properties and are, therefore, intended in the definition of glass fibers. Irrespective of the type of glass, as is well known, glass fibers are, on a relative basis as compared with, for example, polymeric textile fibers, quite stiff. While this stiffness tends to result in a loftier structure and, hence, more depth filtration, this also means that it is difficult to ensure that the stiff glass fibers have been entwined sufficiently with the matrix textile fibers to ensure that the matrix glass fibers are interlocked therewith, especially with glass fibers in the higher diameter ranges, e.g. 4 or 5 microns, and especially since current manufactures of these fine glass fibers have considerable differences in the lengths thereof, e.g. the average length of these fibers can be between 0.3 and 3 millimeters or even outside of these ranges. By selecting the glass fibers, e.g. with diameters between about 0.5 and 1 micron, which will have average lengths of between about 0.5 and 1 millimeter, e.g. especially about 0.65 microns in diameter, this difficulty of ensuring interlocking with the matrix textile fibers can be mitigated, but it cannot be avoided altogether.

Also, while the use of sheath/core matrix fibers, as described more fully below, will also mitigate this problem, the problem cannot be altogether avoided thereby. It appears, in this regard, that the thermoplastic, and, hence, heat softenable, sheath, disposed on the relatively large matrix textile fibers (as compared with the size of the glass fibers) is not necessarily capable of fully adhering the much smaller and somewhat mobile matrix glass fibers. In addition, even at relatively low glass fiber percentages, e.g. 5% on a weight basis of the web, the number of these small glass fibers is quite large, and with this large number of relatively stiff, short glass fibers, complete securing by sheath/core matrix fibers is not ensured.

In view of the above, it was found that to ensure the securing of the glass fibers into the web, a separate binder in the web was required. While theoretically this binder could be a thermosetting or thermoplastic binder, it was found that thermosetting binders were not satisfactory for a number of reasons, including the need for a catalyst which may not be compatible with blood filtering, longer reaction times for cross-linking and, hence, prolonged production times, generally uniform distribution thereof throughout the web instead of being concentrated at critical cross-over positions, as explained below, larger amounts to ensure binding of the glass fibers, and a somewhat stiff and boardy filter material. Hence, the binder must be a thermoplastic binder.

In this latter regard, the binder may be any thermoplastic binder which has softening temperatures below those temperature which would adversely affect the matrix textile fibers, e.g. below about 400° F., preferably below 350° F., and especially below about 300° F. or 250° F. or even below 220° F. In this regard, softening temperature is defined as that temperature at which the thermoplastic binder sufficiently softens so as to adhere to both the matrix textile fibers and the matrix glass fibers. However, it was found that certain thermoplastic binders have special advantages, in that the binders either have particularly good adherence to these fibers or tended to migrate to fiber cross-over positions, as explained below, or both.

These thermoplastic binders are polyvinyl acetate, polyvinyl chloride, polyacrylics and acrylates, polyacrylonitrile, polybutadiene, polyethylene, polyisoprene, polyvinyl acetate ethylene, polyvinyl acetate acrylate and polystyrene-butadiene. It is also possible to use desolubilized gums such as polyvinyl alcohol and cellulose gum, but the desolubilized versions of these water-soluble gums are much more difficult to ensure sufficient desolubilization and are therefore not preferred. These binders may be applied to the web prior to or during formation thereof and as powders or solutions, but it has been found that very special advantages are provided when the binders are applied to the already formed web and as an emulsion.

In this regard, as can be seen from FIG. 2, in order to ensure that the matrix glass fibers 8 are secured to the matrix textile fibers 5, it is only necessary to have the binder at cross-over positions 9. Any other disposition of the binder will not significantly improve the binding of the glass fibers to the textile fibers and will only serve to decrease the filtration throughput. Thus, if the binder could be arranged to be substantially disposed only at these cross-over positions, securing of the glass fibers is ensured and a minimum of stiffening binder may be used.

It was found that if the binder, in emulsion form, is applied to the already formed web, the emulsion sized particles of the binder plastic in the emulsion tend to be more removed from the emulsion at these cross-over positions than at other places throughout the web. Thus, the emulsion form of the binder proved to be a substantially superior form thereof. While not bound by theory, as can be seen from FIG. 2, the cross-over positions constitute the closest physical restraints for removing binder particles from the emulsion. Hence, if the emulsion is in effect filtered through the web, the binder particles 4 will be preferentially removed from the emulsion at these cross-over positions and the retained binder particles are, therefore, in the preferred position in the web for maximum binding of the glass fibers and textile fibers with minimum amounts of binder.

As can be appreciated from the above, this far-preferred filtering action of the binder particles cannot be reasonably achieved with a solution or melt of the binder, but only from a dispersion of the binder. Further, it could not be achieved when the binder is added before or during forming of the web; it can be achieved only after the web is formed. Also, while the dispersion could function even if not in emulsion form, quite obviously, an emulsion form will provide a more uniform dispersion and deposition at the cross-over positions. Hence, it is greatly preferred that the binder is in emulsion form and applied to the formed web.

In this latter regard, the emulsion could be applied to the web by conventional padding or printing of the web with the emulsion, or even immersing the web in the emulsion, but it will also be apparent that the desired filtering action of the binder particles is far more sure when the emulsion is applied to only one side of the web, e.g. by spraying one side of the web, e.g. top side, with the emulsion and with a reduced pressure on the other side of the web. This means of applying the emulsion is also most convenient for use in a conventional web-forming process and apparatus, as discussed more fully below.

In view of the above, certain of the above-described polymeric binders are preferred, since they can easily be formed into stable emulsions. Among these are polyvinyl acetates and acrylates, polyacrylics and acrylates, polybutadiene and polyisoprene, with polyacrylics and acrylates being more preferred.

The emulsion may have solids contents between about 0.1% and 50% and still provide the required filtering action of the binder particles, especially between about 0.5% and 20%, e.g. between about 1% or 5% and 10%. This will also produce an add-on of binder particles to the formed web of about 0.1% to 10%, based on the weight of the web. At about 10% add-ons, the adherence of the glass fibers is well ensured and additional add-ons beyond this amount can cause decreases in pore sizes of the filter material, along with decreased throughput and increased pressure drop. Further, below that 10% add-ons, the flexibility of the finished filter material is not substantially reduced, so long as the binder polymer is flexible at room temperature and has a glass transition temperature of above 100° F. At less than about 0.1% add-ons, the amount of binder is insufficient, although add-ons of about 0.25% or 1% are quite satisfactory.

Figure 4:
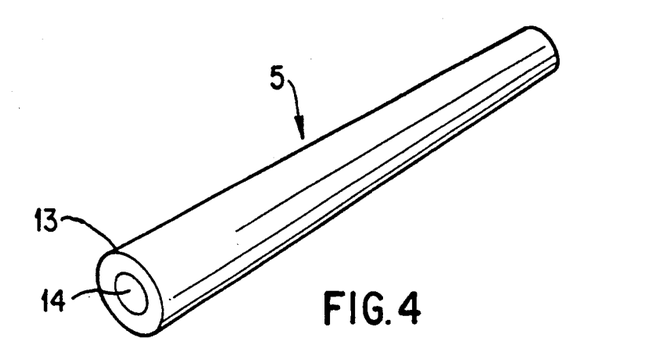
FIG. 4 is a perspective view of an alternate textile fiber useful in the present invention.

As noted above, a portion of the matrix textile fibers 5 may have a sheath 13 and a core 14 (see FIG. 4). The sheath 13 will be of a low melt temperature polymer, and the core 14 will be of a higher melt temperature polymer. For example, the core 14 may be a polyester polymer, and the sheath 13 may be a low-melt olefin, such as polyethylene. When at least a portion of the matrix textile fibers of the filter material are the sheath/core fibers, the web of the filter material, when being processed, is subjected to temperatures such that the web has experienced temperatures sufficient to at least soften the polymer sheath 13 and cause at least some adherence of that softened sheath of the textile fibers 5 to other such fibers and to, at least, part of the matrix glass fibers and the fibrils of the fibrillated particles. As can be appreciated, this will cause a bonding of the matrix textile fibers together, to improve the strength of the interstices, and will cause bonding of the fibrils of the fibrillated particles to the sheath of the textile fibers. This will ensure better locking of the fibrillated particles in the filter material.

While as little as about 1% of the matrix textile fibers may have the sheath thereon, and at least some improvement will be provided for securing the fibrillated particles in the filter material, generally, at least about 5% of the matrix textile fibers should be the sheath/core fibers. On the other hand, while a large percentage of the textile fibers could be the sheath/core fibers, this would render the resulting filter material rather stiff, which is not desired, simply for convenience of handling, and, therefore, it is preferred that the sheath/core textile fibers be no greater than about 30%. At percentages of about 30% or less, there is no significant deterioration in the handling qualities of the filter material. Thus, a preferred range for the sheath/core textile fibers is between about 5% and 30%. Within this range, the filter material so locks the fibrillated particles into the filter material that the filter material can withstand a filtering blood pressure drop of at least five feet of head without substantial displacement of the fibrillated particles from the web.

The sheath/core fibers, if used, may have a denier of about 0.05 to 0.75 denier, but if 30% or less of sheath fibers are used, that denier may be higher, e.g. up to about 3 or 4 denier. For example, when about 10% sheath/core fibers are used, conventional 2 denier sheath/core fibers may be used.

The sheath/core fiber, if used, may have a core of textile fiber material, and the sheath may be any low melting polymer. While a wide range of low melting polymer sheaths are known to the art, including methacrylates, vinyls and the like, polyolefin polymers, such as polyethylene or polypropylene, are preferred, since those polymers provide sheaths with very low softening points, and it is easy to soften those sheaths to provide the required adherence. The thickness of the sheath is essentially immaterial, since the only requirement of the sheath is that there be a sufficient layer of the sheath for adherence to adjacent fibers and fibrillated particles. Thus, the sheath can be from as little as 1% to 50%, e.g. 5 to 30% or 10 to 20% of the core diameter.

The fibrillated particles are particles of a synthetic or natural polymer, and a wide range of such polymers may be used, since it is not the particular polymer but the surface area thereof which is important. However, the polymers must be capable of substantial fibrillation, for the reasons expressed above. Thus, generally, the polymer will be a textile fiber material (polymer), since textile fiber materials, usually, are capable of being fibrillated to a high degree. Any of the textile fiber materials noted above may be used as the fibrillated particles. However, it is preferred that the fibrillated particles be particles of the textile fiber materials of polyester fiber material, acrylic fiber material, nylon fiber material, polyolefin fiber material and cellulosic fiber material, since these materials easily fibrillate to high degrees and provide fibrillated particles with a multitude of fibrils, as described above. These materials also provide fibrils which easily attach to and lock with the matrix textile fibers and/or the glass fibers, with or without sheath/core fibers. Further preferred is where the fibrillated particles are made of a textile fiber material which is predominantly a cellulosic fiber material, since fibrillated particles of that material provide a large number of fibrils, and it is especially preferred that the cellulosic fiber material be cellulose acetate, since a great number of fibrils are produced with that material, and the material has a natural hydrophilic nature and, thus, an affinity for leucocytes.

It is not necessary to describe in detail the fibrillated particles, since these fibrillated particles are known to the art and are commercially available. A full description of such fibrillated particles may be found in U.S. Pat. No. 4,274,914 to Keith, et al, issued on Jun. 23, 1981. That patent describes, in detail, the method of manufacture of the fibrillated particles and the fibrillated particles themselves. Those fibrillated particles have been used in the art as binders, primarily, especially in filter papers, and as especially used for binding adsorbents, such as activated carbon powders, in non-woven media. Among other applications are combustible shell casings, specialty papers, speaker cones, and substitutions for asbestos or aramid fibers in friction materials.

The aforementioned patent, the entire enclosure of which is incorporated herein by reference and relied upon for disclosure herein, also describes applications of the fibrillated particles to cigarette filters and face mask filters, where the fibrillated particles form those filters in combination with various fibers, particularly acetate and polyester fibers. Tobacco smoke filters are particularly described, and the use of the fibrillated particles in forming webs for cigarette-filter purposes is set forth in detail. Accordingly, while a detailed description of the fibrillated particles and the process for producing the present filters need not be set forth in this specification, a brief explanation is set forth below.

Thus, very briefly, those fibrillated particles have overall lengths of less than about 1000 microns and overall widths of about 0.1 to 50 microns, including the fibrils. They are three-dimensional particles, and the depth is approximately equal to the width. These particles are not fibers and cannot be spun into a yarn, i.e. are not textile fibers, e.g. of staple length. They may be best diagrammatically visualized as extremely small "duck down", in the sense of their physical appearance as viewed through a microscope. The fibrils of the particles are extremely small, e.g. generally less than 0.01 micron in diameter and in the order of 1 to 50 microns long. The fibrils radiate from an elongated central portion, but not in any organized fashion.

In all of the above, the textile art terms are used in their common senses. Thus, the term "textile fiber material" is used in its common sense, i.e. that the material, e.g. a polymer, is capable of being formed into a fiber which can be processed by conventional textile machines into a textile material, either woven or non-woven. This, of course, also means that the fibers of the "textile fiber material" must be capable of interlocking among themselves or with other fibers, i.e. a length sufficient that the fibers may be interlocked together to form a yarn or capable of matting to form a non-woven textile or engaged by barbs of needles for producing a needled textile. More usually, this will require a "staple" length of the fibers, i.e. one which allows the fibers to be twisted into a yarn. Of course, the present glass fibers are, therefore, not of a "textile fiber material" in the sense that the present glass fibers are too small to be formed into, e.g., a yarn, and cannot be formed into a woven textile.

The term "textile fiber", likewise means that the fiber is made of a "textile fiber material" and can likewise be formed into a textile, i.e. either woven or non-woven textile. This is opposed to "non-textile fibers", such as the present matrix glass fibers. These glass fibers have very smooth surfaces, are of small diameter and relatively short. Hence, they cannot, with usual textile processes, be spun into a yarn and hence cannot be formed into a woven textile. Neither can they be effectively needled into a non-woven textile, since the smooth surface and stiff character will not allow sufficient interlocking of the glass fibers to form a needled batt of any substantial strength.

Accordingly, the present filter material is made of the larger matrix textile fibers, the small matrix glass fibers (non-textile fibers), the very fine fibrillated particles (non-textile particles) and the binder. The larger matrix textile fibers form major interstices, provide strength to the filter material and hold open the spaces between fibers to allow full use of the high surface area of the fibrillated particles. The smaller matrix glass fibers provide increased surface area to the filter material, as opposed to a filter material where the matrix fibers are all the larger matrix textile fibers, while not significantly decreasing the function of the larger matrix textile fibers.

Figure 5:
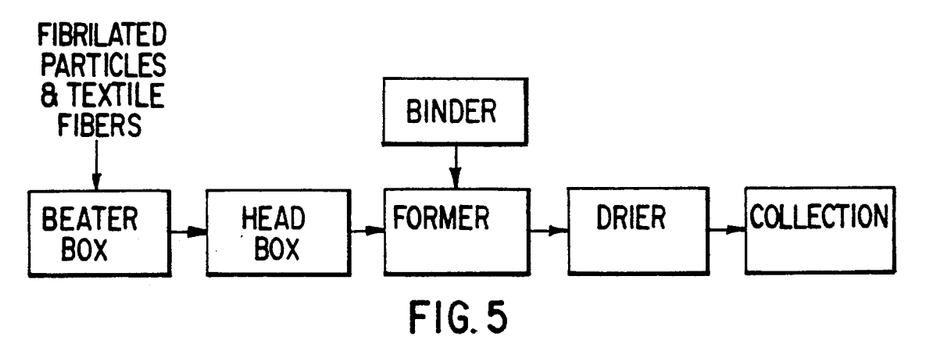
FIG. 5 is a block diagram of the overall preferred process used for making the present filter material.

As shown in FIG. 5, the process, which is a known process and generally described in the above-noted patent, mixes the fibrillated particles, the matrix glass fibers and the matrix textile fibers in a beater box to provide a furnish thereof. While the weight percent of fibrillated particles and fibers to the water in the beater box can vary widely, for most applications of fibrillated particles to be incorporated in the fibers, the total solids content (fibrillated particles and fibers) should be somewhere between about one and five percent. Sufficient mixing in the beater box is conducted until a homogenous slurry of the fibers and particles is obtained.

Thereafter, the furnish slurry is fed to a head box of an ordinary paper-making machine. Of course, if desired, intermediate stock tanks and mixers may be used, depending upon the particular machine and the schedule of processing thereon, all of which is well known in the art. Any of the conventional paper-making machines may be used, e.g. a rotating screen machine, a perforated drum machine, and the like, but a usual Fourdrinier machine is preferable, in view of the simplicity of operation of that machine and the control of the web thickness achieved thereby.

In any event, the furnish slurry of fibrillated particles and fibers is fed from the head box to the former of the machine, whether it be the rotating perforated drum or rotating screen or the Fourdrinier machine, and that slurry of fibers and particles is dewatered, by vacuum, to form a wet web.

After the vacuum is applied to the underside of the web, preferably, the vacuum is discontinued and then the binder emulsion is applied to the top side thereof and preferably the vacuum is thereafter reapplied. This application of the binder can be by way of a padding roll or a squeegy bar or doctor blade, but preferably it is simply sprayed onto the web with conventional spray jets, positioned so as to provide a relatively uniform wetting of the top side of the web by the sprayed emulsion. The conventional subsequently vacuum applied to the underside of the web sucks the emulsion through the web and filters the binder particles therefrom so as to deposit the binder particles predominantly at the cross-over positions, as explained above. No particular degree of vacuum is required, and, indeed, adequate filtering of the binder particles will take place with no vacuum or very high vacuum, e.g. $-12$ lbs. gauge.

That wet web is then passed to a drier, which is usually a series of steam-heated cans, and is heated sufficiently to dry the web and set the binder. In the case of the use of sheath/core fibers, that drying temperature must be sufficient to ensure that the sheath of the sheath/core fibers is sufficiently softened to achieve the bonding, described above. That temperature, of course, will vary with the particular sheath, but, generally speaking, steam-heated cans with steam up to 1 to 2 atmospheres of superheat is more than sufficient to cause such adherence of the usual sheathed fibers, as well as set the binder. If a sheathed fiber is not used, then the steam-heated cans can be at almost any temperature, e.g. 120° F. to 300° F., consistent with setting the binder and drying the web to a relatively low moisture content, e.g. less than 10%, or usually less than 5% or 2% by weight moisture. From there, the dried web is collected in an ordinary collection mechanism, e.g. a roll collecting mechanism, and is then ready for cutting into desired filter shapes.

The setting temperatures for the binder will vary substantially with the particular binder. The setting temperature must be high enough to cause the binder to tackify and adhere to the glass fibers. More preferably, the heat softened binder will be at a temperature high enough to at least partially move or flow to form configured binder pools, as shown in FIG. 2. For most binders, especially the preferred binders, the temperature will be at least 150° F., especially at least 200° F. and as high as 250° to 275° F.

As noted in the parent application, it was found that a modification of that process and the resulting filter material is of advantage. In this regard, it was found that the fibrillated particles have a tendency to agglomerate during the process until the furnish slurry is deposited on the former. In the finished filter material, such agglomeration can cause undesired reduction in surface area and, correspondingly, decreased leucocyte depletion.

It has been found that such agglomeration can be avoided by incorporating into the furnish a small amount of small fibers. These small fibers are of less than staple size, i.e. non-textile fibers, and are used in amounts up to 10%. Amounts as low as 1%, however, are usually adequate. While these small fibers may be any natural or synthetic fibers, such as described above, the parent application points out that small fibers of ceramic and glass, i.e. microfibers, are preferred, e.g. small fibers usually having average diameters of about 0.1 to 2 microns.

While the parent application pointed out that these small fibers are so interlocked with the fibrillated particles that they are not substantially displaceable from the filter material when filtering blood or a blood fraction, it has now been found that these small fibers are displaced more than had been appreciated. Further, as noted above, with sufficient of these fine fibers, an improved blood filtration is provided, so long as the filter material includes the above-described binder. Hence, the present glass fibers function both for the purposes described in the parent application and for the purposes described herein.

As a means of avoiding any non-wetting and, hence, decreased filtration, in the filter material, the filter material may be treated with a small amount of FDA approved wetting agents, which are known to the art, e.g. the Tweens surface active agents.

Figure 6:
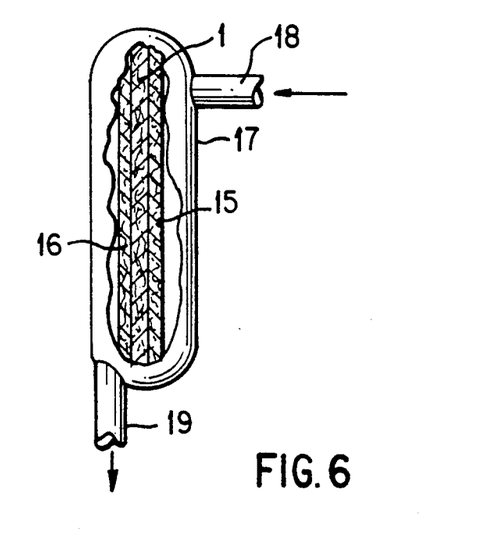
FIG. 6 is a diagrammatic view, partially in broken section, showing a useful, typical, completed filter arrangement, including the filter case.

The filter material may be formed into a filter device in any of the usual manners of the art, and FIG. 6 shows an acceptable example thereof. As shown in FIG. 6, the filter material 1 may be sandwiched between a prefilter 15 and a subsequent filter 16. The prefilter 15 is used to remove large agglomerates and the like which often occur in stored blood, and this prefilter can be any of the usual prefilters known in the art for that purpose. These prefilters can be woven or non-woven textile materials or metal meshes or the like, and the particular prefilter can be chosen as desired.

Similarly, the subsequent filter 16 may be simply a supporting subsequent filter, to give mechanical support to the present filter material and the prefilter. That subsequent filter may be, for example, a woven mesh or a wire mesh, simply to provide support for the pressure drop across the entire filter element (the prefilter, the present filter material and the subsequent filter). Here again, this subsequent filter can be as in the prior art, and no particular details are required in connection therewith.

The filter assembly is held in a conventional housing 17 which has a conventional inlet 18 and a conventional outlet 19. The filter assembly is held in that housing in any convenient manner for mechanically locking the filter element into the housing, e.g. mechanical clamps. Such housing, along with the filter elements therein, is desirably disposable, and with the low cost of the present filter material, such a filter assembly in such a housing is disposable at a low expense.

While FIG. 6 illustrates a convenient and conventional housing and arrangement of the filter elements, any of the other conventional housings and arrangements of filter elements known to the prior art may be used with the present filter material, since the present filter material is amenable to almost any desired configuration.

For certain filtering applications, it is desirable to choose among various properties of the filter material for achieving a desired end result. With the present filter material, choices of properties of filtration are easily obtained. Thus, for example, where the filtration is primarily intended to remove larger particles in the blood, with only a minimum depletion of leucocytes, then the filter material may have a relatively low ratio of fibrillated particles to textile fibers. On the other hand, where a high depletion of leucocytes is required, but the rate of throughput of the blood through the filter is not particularly critical, then a relatively high ratio of the fibrillated particles to textile fibers may be used.

Alternatively, such changes in surface area of the filter material may be achieved by choosing the surface area of the fibrillated particles. Thus, one could achieve such a filter material, as described above, by choosing fibrillated particles with a relatively low surface area, e.g. 10 square meters per gram, or, with the same ratio of fibrillated particles to textile materials, a filter material of high surface area could be achieved by choosing fibrillated particles with a relatively high surface area, e.g. 30 or 50 or 70 square meters per gram.

The preferred method of achieving different properties of the filter material is that of using fibrillated particles with a relatively high surface area, e.g. between about 10 and 60 or more square meters per gram, and adjusting the ratio of fibrillated particles to textile fibers. However, with the present glass fibers, fibrillated particles having surface areas up to 100 square meters per gram may be used and still retain those particles in the filter material.

The invention will now be illustrated by the following examples, where all percentages and parts are by weight, unless otherwise noted, which is the case of the foregoing specification and claims.

EXAMPLE 1

Preparation of Prefilter 3 denier and 6 denier polyester fibers (Dacron Type 54) were carded on separate cards. The carded webs were crossed lapped separately onto a moving conveyor to form a mat with discrete layers of 3 and 6 denier fibers. The mat was needled with a conventional needled-punching machine. The needled mat was hot calendared (350° F.). The 3 denier side of the mat was glazed with a hot (500°–550° F.) knife. This material is Lydall style #CW140 which is a commercial filter material for use in a cardiometry reservoir.

Preparation of Filter Material

A wet laid non-woven was produced in the following manner: 70% Teijin 0.5 denier polyethylene tereptha-late (PET) fibers of about 6 to 7 millimeters average length, 10% of Code 106 microglass fibers (Schuller—formerly Manville) having an average diameter of about 0.65 microns, an average length of about 3 millimeters and an average surface area of about 2.4 square meters per gram, 10% Chisso EKC 2 denier core (polypropylene)/sheath (polyolefin copolymer) fibers of about 5 to 9 millimeters average length and 10% Hoescht-Celanese cellulose acetate "fibrets" (fibrillated particles of textile fiber material) were weighed with adjustments made for the moisture content of the materials. Thus, in this example, most of the matrix fibers are the textile fibers as opposed to the glass fibers. This furnish was placed in a commercial web-forming machine at about 5% in water. The furnish slurry was stirred at high speed for 2 minutes to achieve good dispersion. This slurry was discharged from the dump box to a moving screen. Dewatering by vacuum ($-5$ psig) resulted in the forming of a web on top of a screen wire. An acrylic polymer emulsion of about 48% solids (Rohm & Haas HA8) was diluted to about 0.25% solids and sprayed on the top of the dewatered web to wet the web to excess of saturation. Further dewatering was achieved by using the same vacuum. The web was dried at 250° F. on steam-heated cans to produce the present filter material. The thickness of the filter material was approximately 2 millimeters, and the add-ons of binder was about 5%.

Testing

The dried web and prefilter were die cut to 2.574 inch circles. Five of these were inserted into a test filter rig similar to that shown in FIG. 6, where the prefilter and filter material are clamped together to form a filter media. The filter media was oriented in the vertical direction and the blood entered at the bottom of the filter media and exited at the top (opposite to that shown in FIG. 6). The media was oriented so that blood first encountered the prefilter material (3.0 denier side first).

The rig was connected with tubing to a unit of human packed red cells about 10 days old. 80 gms of packed cells were passed through the filter. The leucocyte level of the filtered blood was reduced by about 99%.

EXAMPLE 2

The same prefilter of Example 1 was used, but the filtering material was made of 85% of the glass fibers, 10% of the sheath/core fibers and 5% of the fibrillated particles of Example 1. Otherwise, the filter material, including the binder, and add-ons were the same as in Example 1. Thus, in this filter material most of the matrix textile fibers were replaced by the matrix glass fibers. Two layers of the filter material and two layers of the prefilter (about 4.5 millimeters thickness in total) were placed in the test rig of Example 1, and the test described therein was carried out. A 99.9% reduction in leucocyte content was achieved, and the two layers of filter material retained only two-fifths of the blood retained by Example 1.

Thus, as this example shows, the glass fibers may replace a large portion of the textile fibers of the filter material, and these higher amounts of glass fibers provide filters with excellent efficiency at low thicknesses.

EXAMPLE 3

The same prefilter of Example 1 was used, but the filter material was made of 75% of the PET fibers, 5% of the fibrets, 10% of the microglass fibers and 10% of the core/sheath fibers. Otherwise, Example 1 was repeated.

This filter was tested according to the American Association of Medical Instrumentation (AAMI) standard ANSI/AAMI BF-7-1989, Section 4.2.3.1.

A control filter material was also made according to this example, but the acrylic polymer emulsion binder was not applied thereto, and this filter material was also tested according to the above-noted standard.

However, in both tests, only a single layer of the filter material was used, as opposed to the multiple layers of Example 1, and the test rig without any filter material therein was tested according to that standard to determine ambient filter contamination.

The ambient filter contamination for the empty test rig had a fiber count of 8; the filter material of this example (having the present binder) had a fiber count of 10; and the control filter material (not having the present binder) had a fiber count of greater than 1200. The difference between a fiber count of 8 and 10 is not significant, but a fiber count of 1200 is high.

As can be seen from the examples, therefore, the present invention significantly improves the efficiency of the filter material, while at the same time reduces the amount of fibers displaced therefrom to substantially zero.

What is claimed is:

1. A filter material for filtering leucocytes from a fraction of or whole blood, comprising:
    a shape-sustaining laid textile web having a thickness of at least about 1 millimeter and a bulk density of between about 0.05 and 0.4 g/cm³, said web having:
    (i) a plurality of interlocked, textile fibers with average deniers between about 0.05 and 0.75 and average lengths between about 3 millimeters and 15 millimeters, said textile fibers being substantially uniformly distributed in said web so as to form a matrix of the textile fibers with spaces between adjacent interstices of interlocked fibers;
    (ii) a plurality of fibrillated particles of polymeric material having a surface area of at least about 5 square meters per gram substantially disposed within said spaces of the matrix, wherein the weight ratio of the fibrillated particles to the textile fibers is between about 1:99 and 40:60;
    (iii) a plurality of glass fibers having an average diameter of between about 0.1 and 5 microns, the amount of glass fibers being about 2% to 85% by weight of said web and the glass fibers forming a part of the matrix; and
    (iv) a thermoplastic binder disposed at least at cross-over positions of said textile fibers and glass fibers, the amount of the binder being about 0.1% to 10% by weight of the web.

2. The filter material of claim 1 wherein said diameter of the glass fibers is about 0.65 micron.

3. The filter material of claim 1 wherein the add-ons of the binder is about 5% to 10%.

4. The filter material of claim 1 wherein the binder is flexible at room temperature and has a glass transition temperature above 100° C.

5. The filter material of claim 1 wherein the binder is selected from the polyacrylics and acrylates and mixtures thereof.

6. The filter material of claim 1 wherein the fibrillated particles have lengths of less than about 1000 microns and widths of about 0.1 to 50 microns.

7. The filter material of claim 1 wherein the web thickness is between about 1 millimeter and 10 millimeters.

8. The filter material of claim 1 wherein the average denier of the matrix textile fibers is between about 0.2 and 0.5, the average length is between about 5 and 10 millimeters and the matrix textile fibers are polyester textile fibers.

9. The filter material of claim 1 wherein the fibrillated particles have a surface area of between about 10 and 100 square meters per gram, the matrix textile fibers are polyester fibers and the weight ratio of fibrillated particles to polyester fibers is between about 5:95 and 15:85.

10. The filter material of claim 1 wherein the matrix textile fibers are one or more of polyester fibers, nylon fibers, olefin fibers, cellulosic fibers, natural fibers, and synthetic fiber.

11. The filter material of claim 10 wherein the matrix textile fibers are predominantly polyester fibers.

12. The filter material of claim 1 wherein the fibrillated particles have lengths of about 5 to 50 microns and widths of about 0.1 to 5 microns.

13. The filter material of claim 12 wherein said surface area of the fibrillated particles is at least 10 square meters per gram and up to 100 square meters per gram and the surface area of the filter material is at least 1.5 square meters per gram.

14. The filter material of claim 1 wherein said diameter of the glass fibers is between about 0.3 and 2.0 microns and the average length of the glass fibers is between about 0.3 to 3.0 millimeters.

15. The filter material of claim 14 wherein said diameter of the glass fibers is between about 0.5 and 1 micron.

16. The filter material of claim 14 wherein said length of the glass fibers is between about 0.5 millimeter and 1 millimeter.

17. The filter material of claim 1 wherein the binder has a softening temperature of below about 400° F.

18. The filter material of claim 17 wherein the binder is emulsifiable and is applied to the web as an emulsion.

19. The filter material of claim 18 wherein the add-ons of the binder is about 0.1% to 10%.

20. The filter material of claim 1 wherein the fibrillated particles are particles of a textile fiber material selected from the group consisting of polyester fiber material, acrylic textile material, nylon fiber material, polyolefin fiber material and cellulosic fiber material.

21. The filter material of claim 20 wherein the textile fiber material of the fibrillated particles is predominantly cellulosic fiber material.

22. The filter material of claim 21 wherein the cellulosic fiber material is cellulose acetate.

23. The filter material of claim 1 wherein the matrix textile fibers are so interlocked together and the fibrillated particles are so interlocked to the matrix textile fibers that said filter material can withstand a filtering blood pressure drop of at least 2 feet of head without substantial displacement of the fibrillated particles from the web.

24. The filter material of claim 23 wherein at least a portion of the matrix textile fibers have a sheath of low melt temperature polymer thereon and the web has experienced a temperature sufficient to at least soften said polymer and cause at least some adherence of the matrix textile fibers to other of the matrix textile fibers and to the fibrils of the fibrillated particles.

25. The filter material of claim 24 wherein from about 1% to about 30% of the matrix textile fibers have said sheath thereon.

26. The filter material of claim 25 wherein from about 5% to about 30% of the matrix textile fibers have said sheath thereon and the filter material can withstand a filtering blood pressure drop of at least 5 feet of head without substantial displacement of the fibrillated particles from the web.

* * * * *